United States Patent [19]

Seyed-Bolorforosh

[11] Patent Number: 5,423,319
[45] Date of Patent: Jun. 13, 1995

[54] INTEGRATED IMPEDANCE MATCHING LAYER TO ACOUSTIC BOUNDARY PROBLEMS FOR CLINICAL ULTRASONIC TRANSDUCERS

[75] Inventor: Mir S. Seyed-Bolorforosh, Palo Alto, Calif.

[73] Assignee: Hewlett-Packard Company, Palo Alto, Calif.

[21] Appl. No.: 260,391
[22] Filed: Jun. 15, 1994
[51] Int. Cl.⁶ ............................................. A61B 8/00
[52] U.S. Cl. ............................................. 128/663.01
[58] Field of Search ............... 128/660.06, 660.08, 128/660.09, 662.03, 663.01; 73/861.25, 642, 644, 603

[56] References Cited

U.S. PATENT DOCUMENTS

| | | | |
|---|---|---|---|
| 2,716,708 | 8/1955 | Bradfield | 310/9.6 |
| 3,387,235 | 6/1966 | Fair | 333/30 |
| 3,718,898 | 2/1973 | Cook et al. | 367/157 |
| 3,833,825 | 9/1975 | Haan | 310/9.5 |
| 4,097,835 | 6/1978 | Green | 367/150 |
| 4,211,948 | 7/1980 | Smith et al. | 310/322 |
| 4,391,281 | 7/1983 | Green | 128/663.01 |
| 4,460,841 | 7/1984 | Smith et al. | 310/334 |
| 4,462,092 | 7/1984 | Kawabuchi et al. | 367/105 |
| 4,542,653 | 9/1985 | Liu | 367/105 |
| 4,672,591 | 6/1987 | Breimesser et al. | 367/152 |
| 4,692,654 | 9/1987 | Umemura et al. | 310/334 |
| 4,717,851 | 2/1988 | Fenner et al. | 310/334 |
| 4,722,346 | 2/1988 | Chen | 128/662.03 |
| 4,888,861 | 12/1989 | Day | 310/322 |
| 5,002,058 | 3/1991 | Martinelli | 128/662 |
| 5,030,874 | 7/1991 | Saito et al. | 310/334 |
| 5,045,746 | 9/1991 | Wersing et al. | 310/334 |
| 5,048,529 | 9/1991 | Blumenthal | 128/660.1 |
| 5,050,610 | 9/1991 | Oaks et al. | 128/660.01 |
| 5,053,008 | 10/1991 | Bjaj | 604/104 |
| 5,070,882 | 12/1991 | Bui et al. | 128/662.06 |
| 5,090,414 | 2/1992 | Takano | 128/662.05 |
| 5,099,459 | 3/1992 | Smith | 367/153 |
| 5,115,809 | 5/1992 | Saitoh et al. | 128/662.03 |
| 5,115,810 | 5/1992 | Watanabe et al. | 128/662.03 |
| 5,142,187 | 8/1992 | Saito et al. | 310/358 |
| 5,175,709 | 12/1992 | Slayton et al. | 367/90 |
| 5,181,514 | 1/1993 | Solomon et al. | 128/660.09 |
| 5,186,177 | 2/1993 | O'Donnell et al. | 128/662.06 |
| 5,190,045 | 3/1993 | Frazin | 128/662.06 |
| 5,203,337 | 4/1993 | Feldman | 128/662.06 |
| 5,235,553 | 8/1993 | Garlick et al. | 128/663.01 |
| 5,237,542 | 8/1993 | Burke et al. | 367/103 |
| 5,255,684 | 10/1993 | Rello | 128/662.06 |
| 5,271,406 | 12/1993 | Ganguly et al. | 128/663.01 |
| 5,273,045 | 12/1993 | Chihara et al. | 128/662.06 |

FOREIGN PATENT DOCUMENTS 90305961  5/1990  European Pat. Off. ........ B06B 1/06

OTHER PUBLICATIONS

M. I. Haller and B. T. Khuri-Yakub, "Micromachined Ultrasonic Materials", 1991 Ultrasonics Symposium, 1991, IEEE, pp. 403-405.

Wallace Arden Smith and Bertram A. Auld, "Modelling 1-3 Composite Piezoelectrics: Thickness-Mode Oscillations", IEEE Transation on Ultrasonics, Ferrolectrics, and Frequency Control, vol. 338, No. 1, Jan., 1991, pp. -40-47.

R. E. Newnham, D. P. Skinner and L. E. Cross, "Connectivity and Piezoelectrics-Pyroelectric Composites", Material Research Bulletin, vol. 13, 1978, pp. 525-536.

G. S. Kino, "Acoustic Waves", pp. 41-45.

George K. Lewis, "A Matrix Technique for Analyzing the Performance of Multilayered Front Matched and Backed Piezoelectric Ceramic Transducers", Acoustic Imaging, No. 8, 1978, pp. 395-416.

*Primary Examiner*—George Manuel

[57] ABSTRACT

An ultrasonic probe for providing efficient and controlled acoustic coupling to a desired medium under examination by the probe. The ultrasonic probe of the present invention employs one or more ultrasonic transducers substantially surrounded by a fluid. The ultrasonic transducer is acoustically coupled to the fluid for transmitting the beam of acoustic signals therethrough. A housing that is acoustically coupled with the fluid substantially encloses the fluid and the transducer. The housing comprises a layer portion of a material contiguous with a bulk remainder portion of the material. Additionally, an impedance matching means is integral with the housing for controlling an acoustic impedance of the layer portion of the housing.

13 Claims, 8 Drawing Sheets

INTEGRATED IMPEDANCE MATCHING LAYER TO ACOUSTIC BOUNDARY PROBLEMS FOR CLINICAL ULTRASONIC TRANSDUCERS

FIELD OF THE INVENTION

The invention generally relates to ultrasonic medical imaging systems and move particularly to probes used in conjunction with such ultrasonic medical imaging equipment.

BACKGROUND OF THE INVENTION

Ultrasonic probes provide a convenient and accurate way of gathering information about various structures of interest within a body being analyzed. In general, the various structures of interest have acoustic impedances that are different than an acoustic impedance of a medium of the body surrounding the structures. In operation, such ultrasonic probes generate a signal of acoustic waves that is then acoustically coupled from the probe into the medium of the body so that the acoustic signal is transmitted into the body. As the acoustic signal propagates through the body, part of the signal is reflected by the various structures within the body and then received by the ultrasonic probe. By analyzing a relative temporal delay and intensity of the reflected acoustic waves received by the probe, a spaced relation of the various structures within the body and qualities related to the acoustic impedance of the structures can be extrapolated from the reflected signal.

For example, medical ultrasonic probes provide a convenient and accurate way for a physician to collect imaging data of various anatomical parts, such as heart tissue or fetal tissue structures within a body of a patient. In general, the heart or fetal tissues of interest have acoustic impedances that are different than an acoustic impedance of bodily fluids surrounding the tissue structures. In operation, such a medical probe generates a signal of acoustic waves that is acoustically coupled from the probe into the medium of the patient's body, so that the signal is transmitted into the patient's body.

In a catheter-type probe, capable of imaging inside of a blood vessel or artery, acoustic coupling is achieved by inserting the probe into the patient's body and through the blood vessel or artery. For example the probe includes a probe housing that contains an ultrasonic transducer. The transducer generates a beam of acoustic signals, which are transmitted through the probe housing. The ultrasonic beam scans the interior of the blood vessel.

In other cases, such as vaginal or trans-esophageal probes, acoustic coupling is achieved by inserting the probe into a bodily orifice. Alternatively, with abdominal probes, less invasive means are used to achieve acoustic coupling, such as pressing the front portion of the probe into contact with a surface of the abdomen of the patient.

Typically, such probes are mechanically scanned by moving an ultrasonic transducer within the probe. For example, a front portion of such a probe includes a hemispherical housing that contains a moveable ultrasonic transducer. The housing is pressed into contact with a patient's tissue during operation of the probe. A beam of acoustic signals generated by the transducer is transmitted through the housing so as to analyze the patient's tissue. A motor coupled to the transducer causes the transducer to mechanically scan back and forth, so as to sweep the beam of acoustic signals through the patient's tissue.

In general, as the acoustic signal propagates through the patient's body, portions of the signal are weakly reflected by the various tissue structures within the body and received by the ultrasonic medical probe. As the weakly reflected acoustic waves propagate through the probe, they are electrically sensed by electrodes coupled thereto. By analyzing a relative temporal delay and intensity of the weakly reflected waves received by the medical probe, imaging system components that are electrically coupled to the electrodes extrapolate an image from the weakly reflected waves to illustrate spaced relation of the various tissue structures within the patient's body and qualities related to the acoustic impedance of the tissue structures. The physician views the extrapolated image on a display device coupled to the imaging system.

Since the acoustic signal is only weakly reflected by the tissue structures of interest, it is important to try to provide efficient acoustic coupling between the probe and the medium of the patient's body. Such efficient acoustic coupling would insure that strength of the acoustic signal generated by the probe is not excessively diminished as the signal is transmitted from the probe into the medium of the body. Additionally, such efficient acoustic coupling would insure that strength of the weakly reflected signal is not excessively diminished as the reflected signal is received by the probe from the medium of the body.

An impediment to efficient acoustic coupling is an acoustic impedance mis-match between an acoustic impedance of a material of the probe housing and an acoustic impedance of the medium under examination by the probe. For example, one material for the probe housing is acrylic plastic, which has an acoustic impedance of approximately $3.26*10^6$ kilograms/meter$^2$-second, kg/m$^2$s. The acoustic impedance of acrylic plastic is mis-matched with an acoustic impedance of human tissue, which has a value of approximately $1.5*10^6$ kg/m$^2$s.

What is needed is an ultrasonic probe that provides enhanced operational performance, while further providing efficient acoustic coupling to the desired medium under examination by the probe.

SUMMARY OF THE INVENTION

An ultrasonic probe of the present invention provides efficient and controlled acoustic coupling to a desired medium under examination by the probe.

Briefly and in general terms, the ultrasonic probe of the present invention employs one or more ultrasonic transducers substantially surrounded by a fluid. The ultrasonic transducer is acoustically coupled to the fluid for transmitting the beam of acoustic signals therethrough. A housing that is acoustically coupled with the fluid substantially encloses the fluid and the transducer. The housing comprises a layer portion of a material contiguous with a bulk remainder portion of the material. Additionally, an impedance matching means is integral with the housing for controlling an acoustic impedance of the layer portion of the housing.

Since the medium under examination by the probe and the material of the housing each have different respective acoustic impedances, the ultrasonic probe efficiently couples a beam of acoustic signals between the probe and the medium by controlling an acoustic impedance of the layer so as to substantially match the acoustic impedance of the housing material with an acoustic impedance of the medium. Preferably, shallow grooves extending only through the layer portion of the material are used to control the acoustic impedance of the layer portion of the housing. More specifically, the shallow groves are micro-grooves, typically extending into the respective face of each element less than 1000 microns. In general, a depth dimension of the grooves is selected to be approximately a quarter of a wavelength of the acoustic signals.

A groove volume fraction of the layer is selected to control acoustic impedance of the layer so as to substantially provide the desired acoustic impedance match. In an illustrative medical imaging application, each groove has a respective volume selected so that the layer substantially provides the desired acoustic impedance match between the acoustic impedance of the material of the housing and an acoustic impedance of a desired medium such as a patient's body.

A manufacturing advantage associated with the present invention is that the grooves can be easily etched, cut or molded into a wide ranges of materials with a controlled groove shape. Furthermore, because the layer providing impedance matching is integral with the housing, the present invention provides the acoustic impedance matching without being burdened by manufacturing and reliability problems that are associated with adhesively bonding layers of dissimilar materials to a housing. Additionally, in the preferred embodiment, high frequency performance of the ultrasonic probe of the present invention is not limited by any adhesive bond lines.

Other aspects and advantages of the present invention will become apparent from the following detailed description, taken in conjunction with the accompanying drawings, illustrating by way of example the principles of the invention.

DETAILED DESCRIPTION OF PREFERRED EMBODIMENT

Figure 1A:
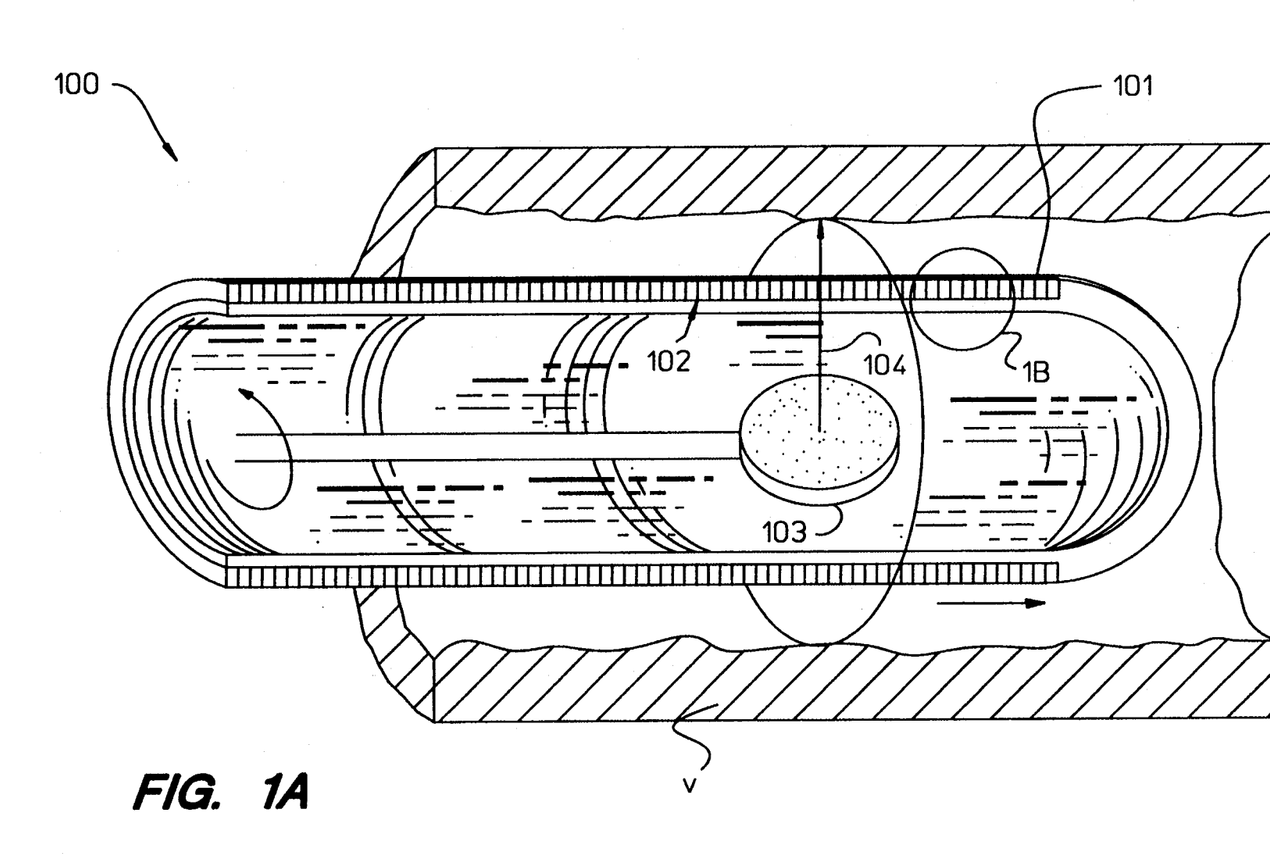
FIG. 1A is a cut away perspective view of a preferred embodiment of the present invention.

The ultrasonic probe of the present invention provides efficient and controlled coupling of an acoustic signal between the probe and the desired medium under examination, and further provides manufacturing, reliability and performance advantages. FIG. 1A is a simplified cut away perspective view illustrating a preferred embodiment of the ultrasonic probe 100. As shown, the preferred embodiment of the ultrasonic probe includes a probe housing 101. The probe housing substantially encloses a rotatable ultrasonic transducer 103 and a fluid, preferably water, that surrounds the transducer. Alternatively, a suitable oil or other liquid may be used as the fluid.

Preferably, the invention is embodied as a catheter probe for imaging inside of a blood vessel or artery. For example, as shown in FIG. 1A, a front portion of the probe housing 101 is inserted into a blood vessel V. Preferably, the housing is substantially shaped like a hollow cylinder having closed ends, however the housing may be shaped otherwise with beneficial results. It should be understood that the housing 101 is shown in cut away view in FIG. 1A to reveal how the fluid and transducer are disposed within the housing.

The transducer generates a beam of acoustic signals 104, which are transmitted through the fluid that surrounds the transducer and through the probe housing. By revolving the transducer as shown in FIG. 1A, the ultrasonic beam 104 scans the tissue of the interior of the blood vessel V. Preferably, the ultrasonic transducer includes a body of piezoelectric ceramic material having a bulk acoustic resonant frequency that determines the frequency of the acoustic signals. A pair of electrodes is disposed on opposing sides of the piezoelectric body for applying a voltage that generates the acoustic signals within the piezoelectric ceramic. Similarly the electrodes sense a voltage produced by reflected acoustic signals received by the piezoelectric ceramic. The electrodes are coupled to imaging system components for extrapolating an image of the tissue from acoustic signals reflected by the tissue.

The housing comprises a layer portion 102 of a material contiguous with a bulk remainder portion of the material. The material of the housing has a bulk acoustic impedance, $Z_{HOUSING}$. Shallow grooves extend through the layer. In the preferred embodiment, the grooves substantially encircle a circumference of the probe housing.

Figure 1B:
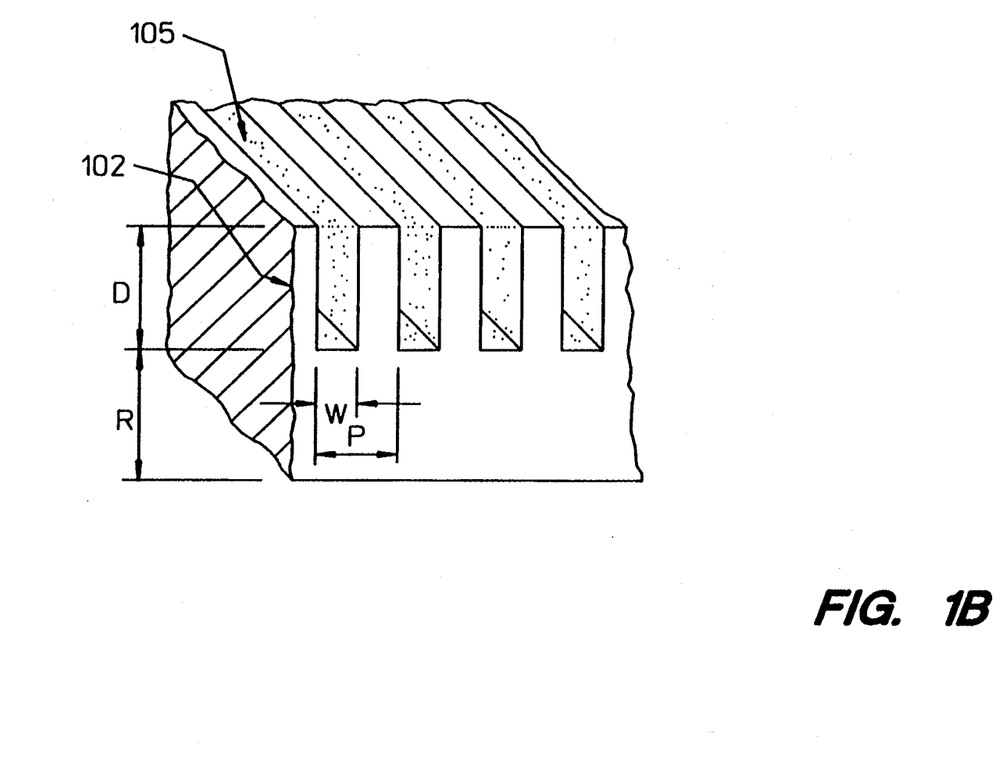
FIG. 1B shows a detailed cut away perspective view of FIG. 1A.

FIG. 1B shows a detailed cut away perspective view of the probe of FIG. 1A. As shown in FIG 1B, the layer has a layer thickness defined by a depth dimension, D, of the shallow grooves extending through the layer. As shown, the bulk remainder portion of the material has a bulk remainder dimension, R.

In the preferred embodiment, the probe housing is essentially embodied in specially contoured enclosure made of an acrylic plastic material. It should be understood that although plastic is preferred, other materials known to those skilled in the art, such as nylon, may be alternatively employed in accordance with the principles of the present invention, with beneficial results.

Preferably, the housing is made by injection molding. The acrylic plastic is injected into a suitable mold having desired groove contours. In the preferred embodiment, the acrylic plastic is first cast in the mold as a sheet having the grooves. The sheet is removed from the mold and rolled into a hollow cylindrical shape so that two ends of the sheet meet at a seam extending along a longitudinal dimension of the cylinder. The seam is then sealed using ultrasonic welding. Similarly, additional members are welded to the cylinder as needed to complete the housing. Alternatively, rather than casting the acrylic plastic of the housing as a sheet, the plastic may be cast as a cylinder having the grooves or as some other shape having the grooves.

Although it is preferred that the groves be molded into the housing material, the grooves may be made using alternative methods. For example the grooves are alternatively cut into the material of the housing using a laser beam. As another alternative, the material of the housing is suitably masked and the grooves etched into the material of the housing using an etchant.

While it is preferred that the grooves substantially encircle the circumference of the housing, in some alternative embodiments the grooves are differently arranged. For example, in these alternative embodiments the grooves are substantially straight, extending along a longitudinal dimension of the housing. In these alternative embodiments the housing is preferably made by extruding melted acrylic plastic in a tube shape through a die nozzle. The die nozzle is shaped so as to impress the straight grooves onto the housing as the longitudinal dimension of the housing is extruded through the nozzle.

In the preferred embodiment shown in FIGS. 1A and 1B, the layer 102 substantially provides an acoustic impedance match between the bulk acoustic impedance of the housing material and the acoustic impedance of a desired medium under examination. For example, in medical imaging applications, the layer substantially provides an acoustic impedance match between the bulk acoustic impedance of the housing material and the acoustic impedance of a medium such as tissue of a patient's body under examination by the probe. As shown in detailed view 1B, the layer 102 includes the grooves 105. In the preferred embodiment, the grooves are substantially circular and arranged approximately parallel to one another along a longitudinal dimension of the housing.

A conformal material, preferably silicone rubber, is disposed within the grooves. A suitable alternative conformal material, for example polyethylene, may be used instead of silicone rubber. The selected conformal material has an acoustic impedance, $Z_{conformal}$, associated therewith.

As the acoustic signals propagate through the tissue of the patient's body, portions of the signal are weakly reflected by the tissue structures within the body, are received by the ultrasonic transducer and are electrically sensed by the pair of electrodes coupled to the ultrasonic transducer. The reflected acoustic signals are first received by the layer portion of the housing material and then propagate through the remainder portion of the housing material. Accordingly, the acoustic signals propagate through the layer with a first velocity, and then propagate through the bulk remainder portion with a second velocity. It is preferred that the depth dimension, D, of the grooves of the layer be selected to be a quarter of a wavelength of the acoustic signals traveling through the layer with the grooves.

The depth dimension, D, of the grooves defines thickness of the layer. The depth dimension, D, of each groove and a pitch dimension, P, of the respective grooves are selected to separate lateral and shear resonance modes of the layer from undesired interaction with the longitudinal resonance mode of the housing. Furthermore, the depth and pitch of the grooves are selected to provide efficient transfer of acoustic energy through the layer. Additionally, the depth and pitch of the grooves are selected so that the layer appears homogenous to acoustic waves. In general, beneficial results are produced by a pitch to depth ratio, P/D, of less than or equal to approximately 0.4, in accordance with additional groove teachings of the present invention discussed in greater detail later herein.

Acoustic impedance of the layer is controlled so as to substantially provide an acoustic impedance match between the bulk acoustic impedance of the housing material and an acoustic impedance of the medium under examination by the probe. Accordingly, the layer provides for efficient acoustic coupling between the probe and the medium under examination. The acoustic impedance of the layer is substantially determined by a groove volume fraction of the layer. The groove volume fraction is based upon the width and pitch dimensions of the grooves 105.

A desired acoustic impedance of the layer, $Z_{layer}$, is calculated to substantially provide an impedance match between the bulk acoustic impedance of the housing material, $Z_{HOUSING}$, and the acoustic impedance of the desired media, $Z_{tissue}$, using an equation:

$$Z_{layer} = (Z_{HOUSING} * Z_{tissue})^{\frac{1}{2}}$$

For example, given that the acoustic impedance of tissue, $Z_{tissue}$, is $1.5*10^6$ kilograms/meter$^2$second, kg/m$^2$s, and that the bulk acoustic impedance of acrylic plastic material of the housing, $Z_{HOUSING}$, is $3.26*10^6$ kg/m$^2$s, the desired acoustic impedance of the layer, $Z_{layer}$, is calculated to be approximately $2.21*10^6$ kg/m$^2$s.

The acoustic impedance of the layer is substantially controlled by the groove volume fraction of the layer. Another relevant factor is an acoustic impedance of the conformal material disposed in the grooves. The groove volume fraction of the layer is defined by dividing a volume of a groove extending through the layer by a sum of the volume of the groove and a volume of remaining layer material adjacent to the groove. A desired groove volume fraction, v, is calculated from the desired acoustic impedance of the layer and respective acoustic impedances of the acrylic plastic, and the conformal material. The desired volume fraction, v, of the groove is approximately equal to an expression:

$$(Z_{HOUSING} - Z_{layer})/(Z_{HOUSING} - Z_{conformal})$$

For example, given silicone rubber as the conformal material having an acoustic impedance, $Z_{conformal}$, of $15*10^6$ kg/m$^2$s and given values for the acoustic impedance of the layer, $Z_{layer}$, and the acoustic impedance of the acrylic plastic material of the housing, $Z_{HOUSING}$, as articulated previously herein, the desired groove volume fraction of the layer, v, is approximately 59.6%. A volume fraction of the layer of the housing complements the groove volume fraction. Accordingly, for this example, the volume fraction of the layer is approximately 40.4%.

A desired depth of the grooves, D, is calculated from a speed of sound in the layer, $C_{layer}$, and a quarter wavelength of a frequency, f, of the acoustic signals, using an equation:

$$D = \frac{1}{4}(C_{layer}/f)$$

Given that the desired groove volume fraction of the layer is approximately 59.6%, speed of sound in the layer with the grooves, $C_{layer}$, can be estimated as being approximately 1900 meters/second. Since a desired frequency, f, of the acoustic signals is 2 megahertz, MHz, the depth of the grooves, D, is approximately 237.5 microns. Accordingly, the grooves are shown to be micro-grooves, extending into the layer less than 1000 microns.

A pitch, P, of the grooves is calculated so that the pitch is less than 0.4 of the depth of the grooves:

$$P \leq (0.4 * D)$$

For example, given depth of the grooves, D, of approximately 237.5 microns, pitch of the grooves should be less than or equal to 95 microns.

Width of grooves, W, is calculated based upon the pitch, P, the groove volume fraction, v, and a correction factor, k, using an equation:

$$W = P * v * k$$

A desired value for the correction factor, k, is selected based on connectivity of the acrylic plastic of the layer and the conformal material. For the layer having grooves arranged as shown in FIGS. 1A and 1B, the layer has 2—2 connectivity and the correction factor, k, is simply 1. In alternative embodiments, the grooves are alternately arranged so that the layer has a different connectivity, yielding a different correction factor. For instance, in an alternative embodiment, the grooves are arranged so that the layer has a 1-3 connectivity, yielding a different correction factor of 1.25. Given 2—2 connectivity so that the correction factor, k, is 1, given pitch of 95 microns, and given groove volume fraction of 59.6%, the width, W, of the grooves is approximately 56.6 microns.

Preferably, the bulk remainder portion of the material has a bulk remainder dimension, R, that is substantially greater than the depth of the microgrooves. For example, given the depth, D, of approximately 237.5 microns, it is preferred that the bulk remainder portion of the material has a bulk remainder dimension, R, of approximately 2,000 microns.

For embodiments of the probe scaled to operate at a higher resonant frequency, relevant groove dimensions and the bulk remainder dimension are scaled accordingly. For example, for an embodiment of the probe scaled to operate at an acoustic frequency of 20 MHz, relevant groove dimensions of the 2 MHz probe example discussed previously are scaled by a factor of 10. Therefore, for a piezoelectric transducer each having a bulk resonant frequency of 20 MHz and respective piezoelectric layers with grooves arranged for 2—2 connectivity, relevant dimensions of the grooves are scaled down by 10 so as to have pitch of 9.5 microns, width of 5.7 microns, and depth of approximately 23.7 microns. Accordingly, the grooves are once again shown to be microgrooves, extending into the front face of the element less than 1000 microns. The bulk remainder dimension is adjusted to be approximately 700 microns.

In the preferred embodiment, a number of grooves encircling the circumference of the housing and disposed along the longitudinal dimension of the housing is related to the pitch of the grooves and the longitudinal dimension of the housing. Typically, the number of circular grooves disposed along the longitudinal dimension of the housing is approximately between the range of 50 and 200 grooves to produce beneficial impedance matching results. As an example, for a section of the having a longitudinal dimension of 10 wave lengths of the acoustic signal, a preferred respective number of grooves disposed along the longitudinal dimension is approximately 100 grooves. For the sake of simplicity, fewer grooves than 100 grooves are shown in FIGS. 1A and 1B.

Figure 2:
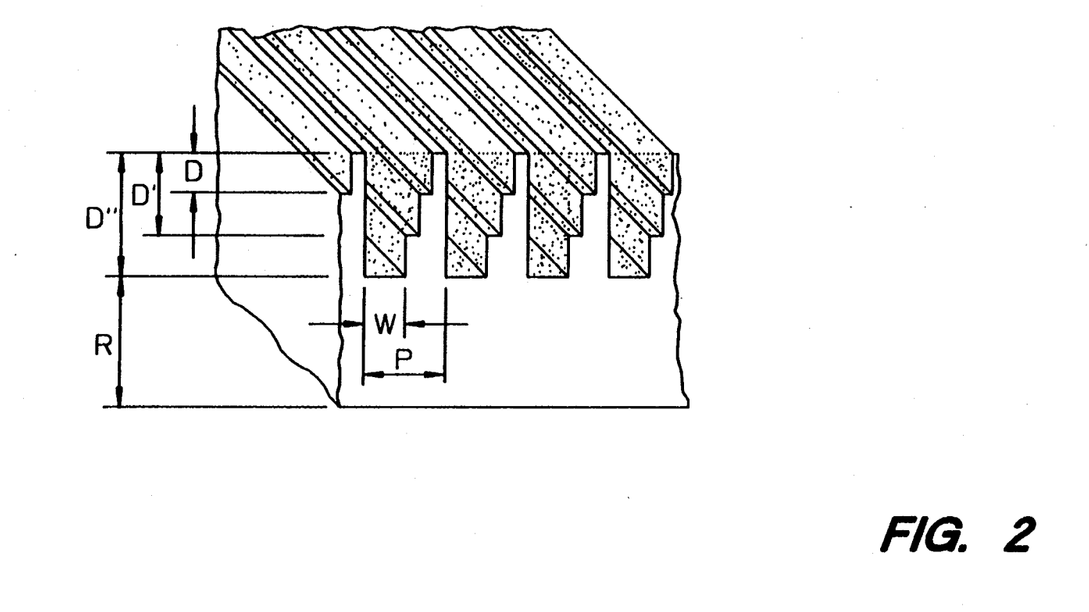
FIG. 2 illustrates an alternative embodiment of grooves extending through a layer of a housing employed in the present invention.

FIG. 2 illustrates an alternative embodiment of grooves extending through a layer of the housing employed in the present invention. As in FIG. 1B discussed previously, FIG. 2 shows grooves extending through the layer, and a bulk remainder portion of the housing material. In contrast to FIG. 1B discussed previously, the grooves of FIG. 2 include a first set of grooves, a second set of grooves, and third set of grooves arranged adjacent one another. As shown, the grooves are arranged so that the grooves have a pitch, P, and a width, W. Each member of the first set of grooves has a respective depth, D, which is approximately equal to an integral multiple of one quarter of a first wavelength of the acoustic signals. Similarly, each member of the second set of grooves has a respective depth dimension, D' which is approximately equal to an integral multiple of one quarter of a second wavelength of the acoustic signals. Each member of a third set of grooves has a respective depth dimension, D" which is approximately equal to an integral multiple of one quarter of a third wavelength of the acoustic signals. Respective members of the first, second and third set of grooves are arranged in a "stair step" pattern as shown in FIG. 2. A single conformal filler material can be deposited in each set of grooves. Alternatively, a different conformal filler material can be deposited in each set of grooves to achieve the desired frequency response. In a similar manner as discussed previously with respect to FIGS. 1A and 1B the housing of the alternative embodiment is made using injection molding.

Figure 3:
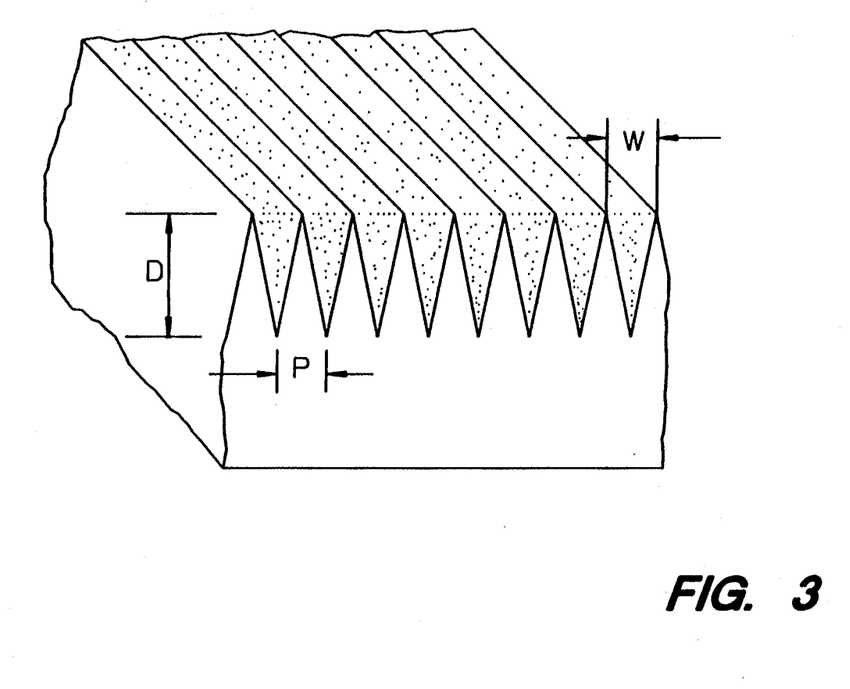
FIG. 3 illustrates another alternative embodiment of grooves extending through the layer of the housing employed in the present invention.

FIG. 3 illustrates another alternative embodiment of grooves extending through the layer of the housing employed in the present invention. A smoothed groove profile is created, in place of the abrupt "stair step" pattern, to provide the layer with enhanced acoustic performance such as broad frequency response or improved acoustic sensitivity. For example, such alternative embodiments include grooves each having a smoothed "V" profile and extending through the layer. Such alternative embodiments are made in a similar manner as discussed previously. As shown, the grooves are created so that the grooves have desired pitch, P, and width, W, and depth, D. In yet additional alternative embodiments, depth of the grooves is varied along the longitudinal dimension of the housing to provide further enhanced frequency response characteristics.

Figure 4A:
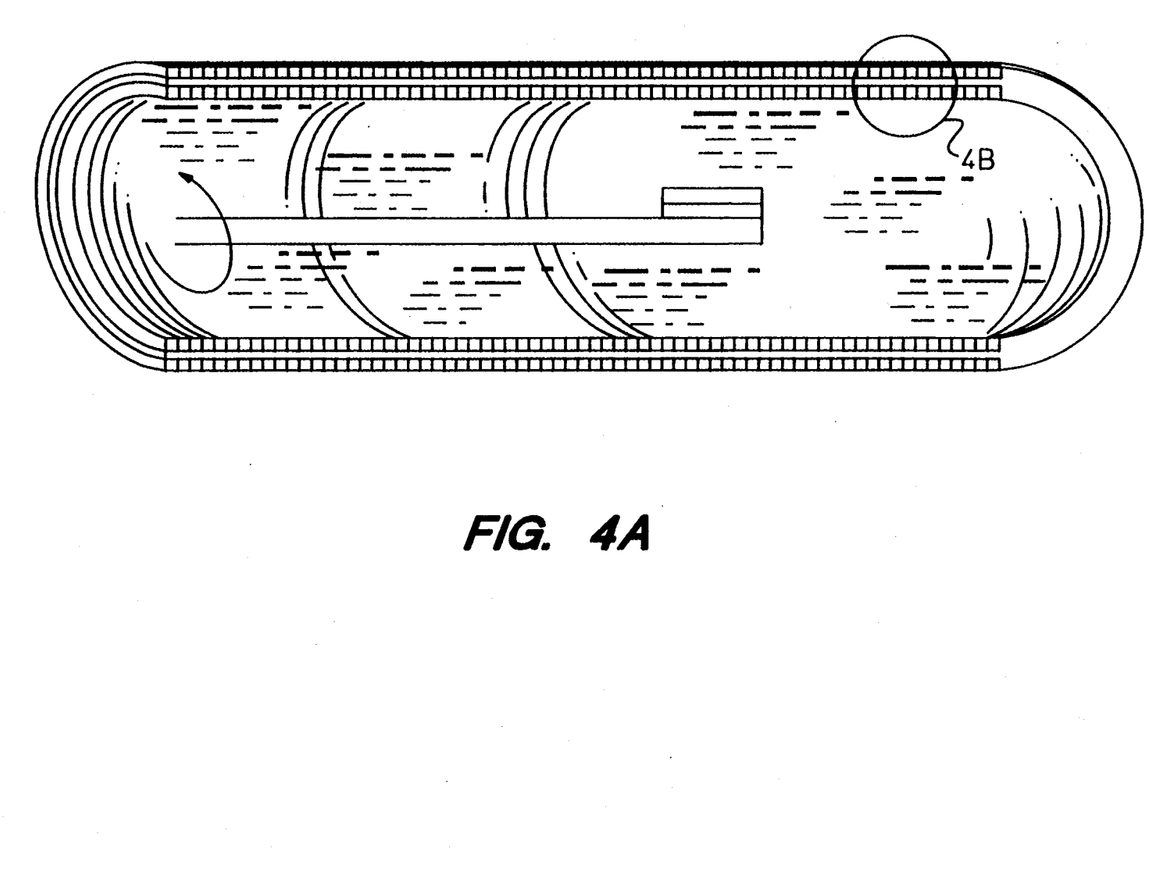
FIG. 4A is a cut away perspective view showing another preferred embodiment of the present invention.

FIG. 4A is a simplified cut away perspective view illustrating another preferred embodiment of the ultrasonic probe. The probe housing substantially encloses a rotatable ultrasonic transducer and a fluid as shown in FIG. 4A. Preferably, the housing is substantially shaped like a hollow cylinder having closed ends, however the housing may be shaped otherwise with beneficial results. It should be understood that the housing is shown in cut away view in FIG. 4A to reveal how the fluid and transducer are disposed with the housing.

The transducer generates a beam of acoustic signals which are transmitted through the fluid that surrounds the transducer and through the probe housing to analyze a media such as human tissue adjacent to the probe. The probe housing is made of a material that has an acoustic impedance. For example, the probe is preferably made of an acrylic plastic, which has an acoustic impedance of approximately 3.26*10⁶ kilograms/meter²second, kg/m²s. Disposed within the housing is the fluid, which has a different acoustic impedance than that of the housing material. For example, it is preferred that the fluid disposed within the housing is water, which has an acoustic impedance similar to that of human tissue, approximately 1.5*10⁶ kg/m²s. Accordingly, the acoustic impedance of material of the housing is mis-matched with the acoustic impedance of the fluid and is also mis-matched with the acoustic impedance of the medium under examination by the probe, such as human tissue.

The invention substantially provides impedance matching of the acoustic impedance of the housing with the acoustic impedance of the fluid so as to decrease reverberation of the acoustic signals within the probe housing. As shown in cut away view in FIG. 4A, the housing comprises an inner layer portion of the housing material contiguous with a bulk remainder portion of the housing material. Shallow grooves extending through the inner layer portion of the housing material control the impedance of the inner layer so as to substantially provide the desired impedance match between the acoustic impedance of the housing and the acoustic impedance of the fluid.

As discussed previously herein, the invention further provides substantial impedance matching of the acoustic impedance of the housing with the acoustic impedance of a media such as human tissue under examination by the probe. As shown in cut away view in FIG. 4A, the housing further comprises an outer layer portion of the housing material contiguous with the bulk remainder portion of the housing material. Shallow grooves extending through the inner layer portion of the housing material control the impedance of the inner layer to substantially provide the desired impedance match between the acoustic impedance of the housing and the acoustic impedance of the media under examination by the probe.

Figure 4B:
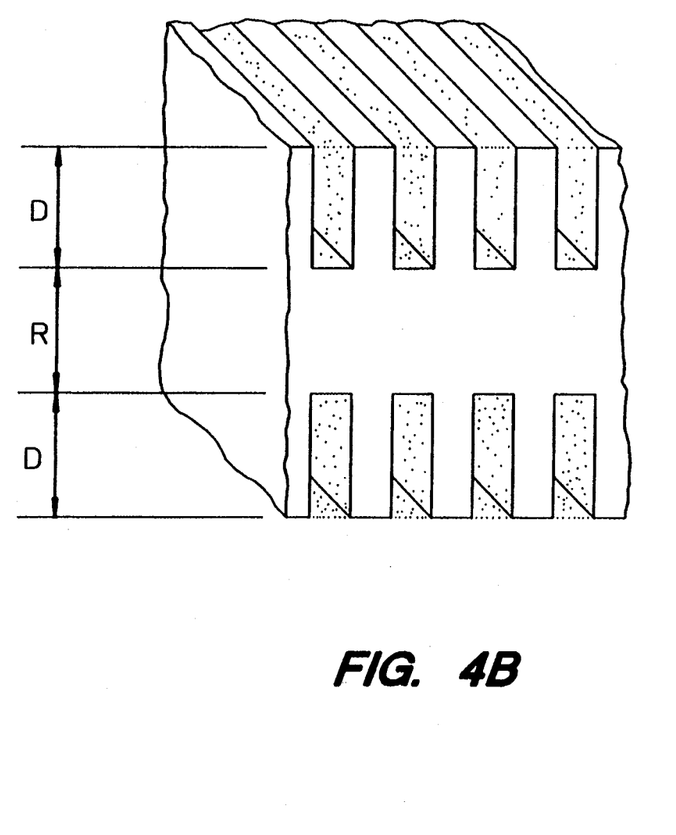
FIG. 4B shows a detailed cut away perspective view of FIG. 4A.

FIG. 4B shows a detailed cut away perspective view of the probe of FIG. 4A. As shown in FIG. 4B, grooves extend a depth, D, through the inner layer of the housing. Additionally, grooves extend a depth D, through the outer layer of the housing. The depth dimensions of the grooves define thicknesses of the layers. The bulk remainder of the housing material has a dimension, R. Dimensions of the grooves are determined in as discussed in detail previously herein with respect to FIGS. 1A and 1B. Preferably, the housing shown in FIGS. 4A and 4B is made by injecting a material such as acrylic plastic into a suitable mold having desired groove contours, in a similar manner as that described previously herein with respect to FIGS. 1A and 1B. As shown in FIG. 4B, a suitable conformal material, such as silicone rubber, is disposed in the grooves.

Figure 4C:
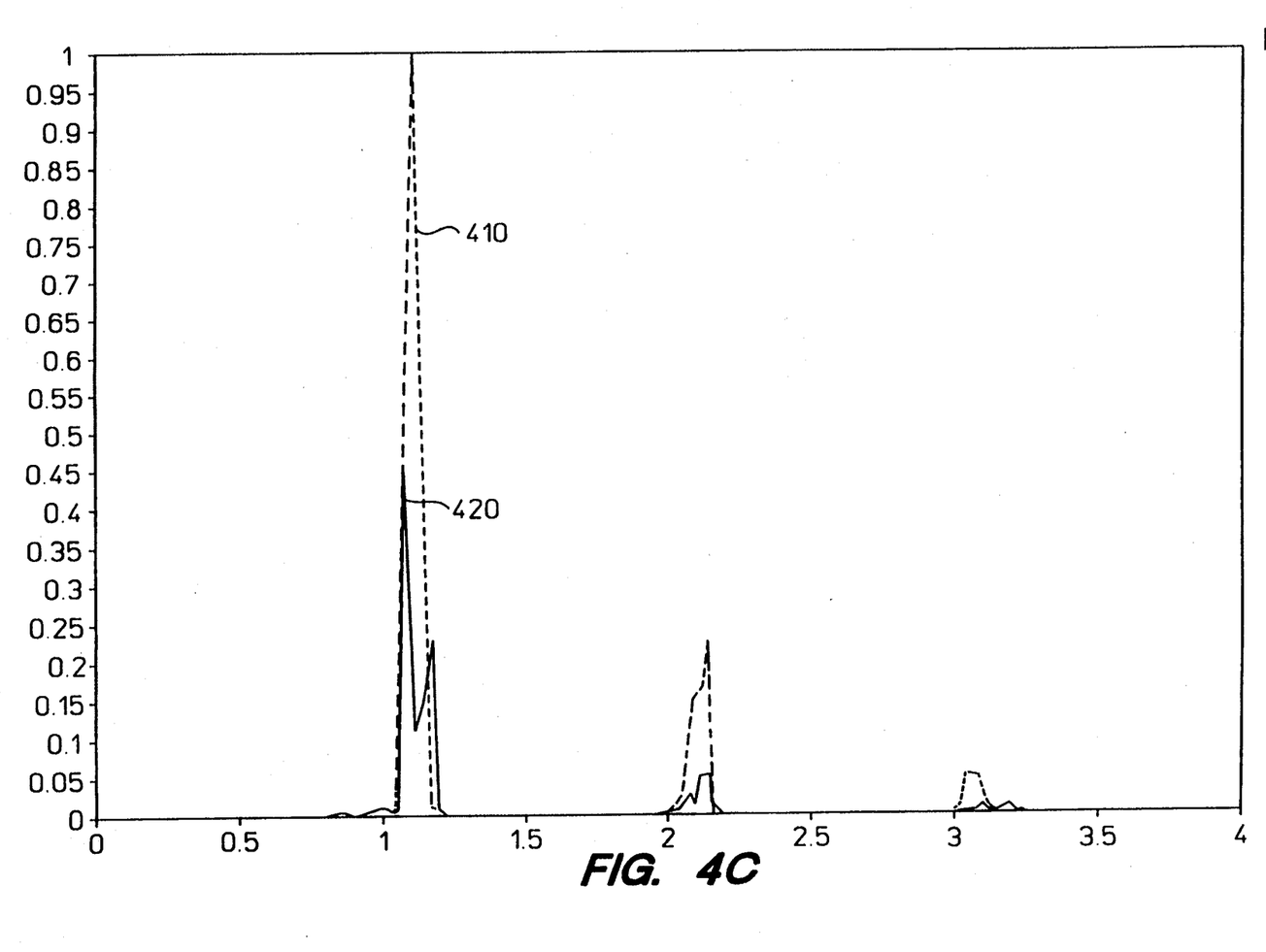
FIG. 4C is a graph illustrating a comparison of internal acoustic reverberations of the embodiment shown in FIG. 1A and the embodiment shown in FIG. 4A.

FIG. 4C is a graph illustrating a comparison of internal acoustic reverberations of the probe shown in FIG. 1A and the probe shown in FIG. 4A. The graph represents rectified impulse responses of each probe, which have been simulated using a digital computer and the Laplace Transform Matrix Method as discussed in "A Matrix Technique for Analyzing the Performance of Multilayered Front Matched and Backed Piezoelectric Ceramic Transducers" by Lewis et al., Acoustic imaging, No. 8, pages 395-416 (1978).

The graph of FIG. 4C shows decreased reverberations in the impulse response of the probe of FIG. 4A, relative to the impulse response of the probe of FIG. 1A. The simulated rectified impulse response of the probe of FIG. 1A is represented by a dashed line 410 in the graph of FIG. 4C. The simulated rectified impulse response of the probe of FIG. 4A is represented by a solid line 420 in the graph of FIG. 4C. Accordingly, as illustrated by the comparison in the graph, the inner layer portion of the probe housing of FIG. 4A advantageously provides substantial impedance matching of the acoustic impedance of the housing with the acoustic impedance of the fluid, so as to decrease reverberation of the acoustic signals within the probe housing.

Figure 5A:
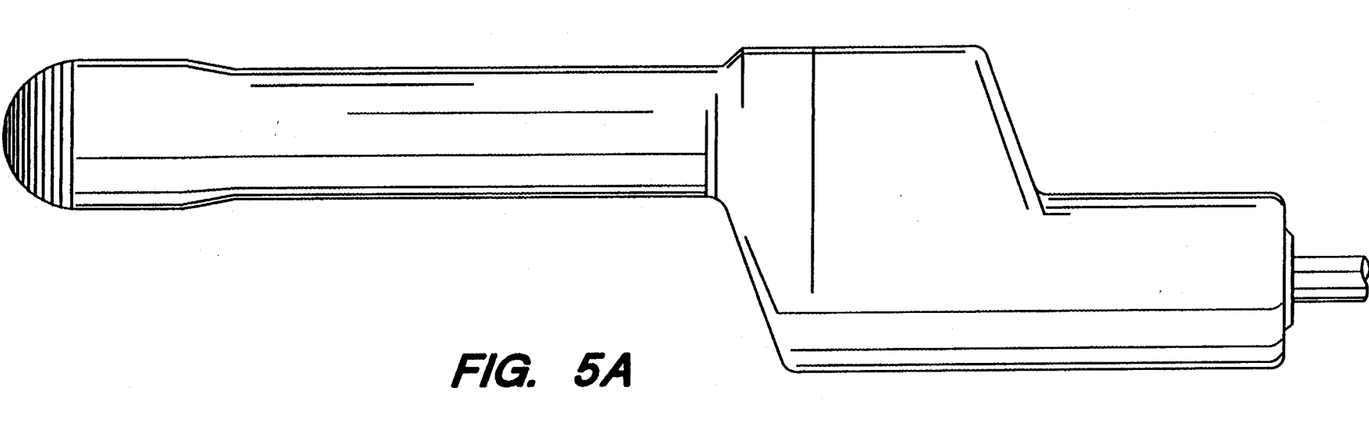
FIG. 5A shows a cut away view of yet another embodiment of the present invention.

FIG. 5A shows a cut away view of another embodiment of the probe of the present invention. As shown, the front portion of the probe includes a substantially hemispherical housing. The housing is pressed into contact with a patient's tissue during operation of the probe. Grooves extending through a layer portion of the housing substantially provide impedance matching as discussed in detail previously herein. As shown, the grooves are arranged so as to be substantially concentric.

Figure 5B:
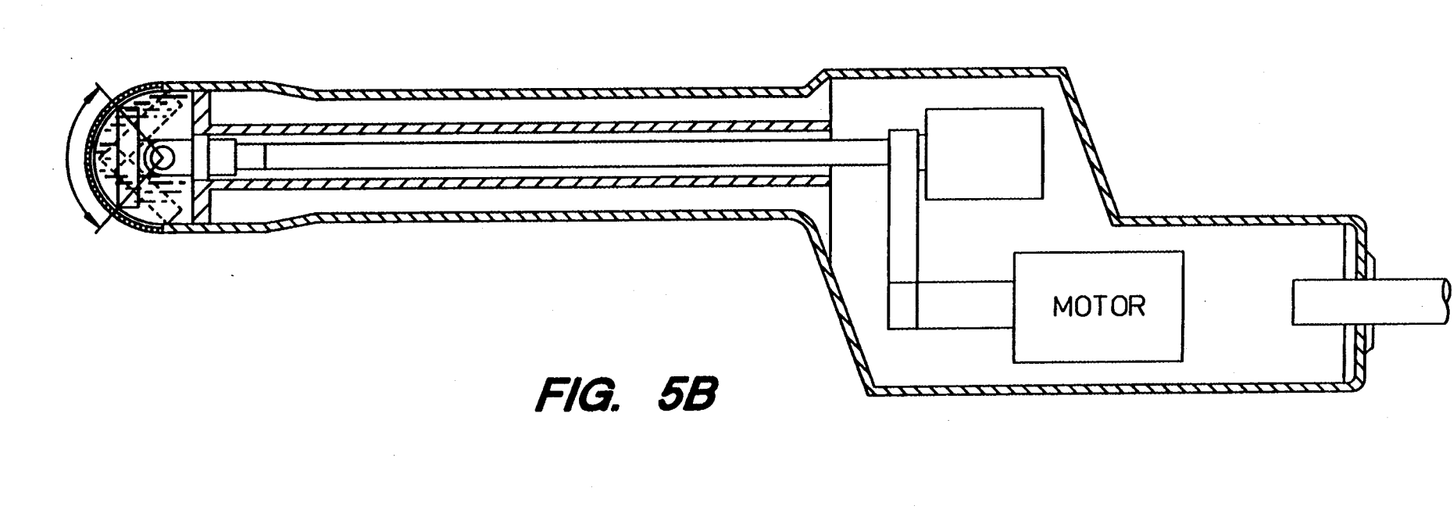
FIG. 5B shows a cut away cross sectional view of FIG. 5A.

FIG. 5B is another view of the probe shown in FIG. 5A, cut away to reveal a mechanically scanned ultrasonic transducer substantially enclosed by the housing. A fluid surrounds the ultrasonic transducer so that a beam of acoustic signals generated by the transducer is transmitted through the fluid and through the housing. A motor is coupled to transducer so as to cause the transducer to mechanically scan back and forth through an arc as shown in FIG. 5B.

As discussed herein, the ultrasonic probe of the present invention provides efficient and controlled acoustic coupling to a desired medium under examination by the probe. Although specific embodiments of the invention have been described and illustrated, the invention is not to be limited to the specific forms or arrangements of parts so described and illustrated, and various modifications and changes can be made without departing from the scope and spirit of the invention. Within the scope of the appended claims, therefore, the invention may be practiced otherwise than as specifically described and illustrated.

What is claimed is:

1. An ultrasonic probe for coupling a beam of acoustic signals between the probe and a medium having an acoustic impedance, the probe comprising:
   a fluid;
   an ultrasonic transducer acoustically coupled to the fluid for transmitting the beam of acoustic signals therethrough;
   a housing substantially enclosing the fluid and the transducer, the housing being acoustically coupled with the fluid, the housing comprising a layer portion of a material contiguous with a bulk remainder portion of the material, the material having an acoustic impedance; and
   an impedance matching means integral with the housing for controlling an acoustic impedance of the layer portion of the housing.

2. An ultrasonic probe as in claim 1 wherein the impedance matching means includes a means for controlling an acoustic impedance of the layer so as to substantially match the acoustic impedance of the housing material with an acoustic impedance of the medium.

3. An ultrasonic probe as in claim 1 wherein:
   the fluid has an acoustic impedance; and
   the impedance matching means includes a means for controlling the acoustic impedance of the layer so as to substantially match the acoustic impedance of the housing material with an acoustic impedance of the fluid.

4. A probe as in claim 1 wherein the impedance matching means includes shallow grooves extending only through the layer portion of the material.

5. An ultrasonic probe as in claim 4 wherein a number of the grooves is within a range of approximately 50 to 200 grooves.

6. An ultrasonic probe as in claim 4 wherein the groves include concentric grooves.

7. An ultrasonic probe as in claim 4 wherein the grooves are substantially circular.

8. An ultrasonic probe as in claim 4 wherein the shallow grooves each have a respective depth dimension approximately equal to one quarter of a wavelength of the acoustic signals.

9. An ultrasonic probe as in claim 4 wherein the grooves include a first and second set of shallow grooves, each member of the first set of shallow grooves have a respective depth dimension that is approximately equal to a quarter of a first wavelength of the acoustic signals, each member of the second set of shallow grooves having a respective depth dimension that is approximately equal to a quarter of a second wavelength of the acoustic signals.

10. An ultrasonic probe as in claim 9 wherein a first conformal material is disposed in the first set of microgrooves and a second conformal material is disposed in the second set of microgrooves.

11. An ultrasonic probe as in claim 4 wherein each of the grooves has a respective volume selected for substantially matching the acoustic impedance of the material with the acoustic impedance of the medium.

12. An ultrasonic probe as in claim 4 wherein each of the grooves has a respective volume selected for substantially matching the acoustic impedance of the material with the acoustic impedance of the fluid.

13. A probe as in claim 1 further comprising a means for moving the transducer within the fluid so as to provide mechanical scanning of the beam of acoustic signals.

* * * * *